(12) United States Patent
Tam

(10) Patent No.: US 6,819,120 B2
(45) Date of Patent: Nov. 16, 2004

(54) NON-CONTACT SURFACE CONDUCTIVITY MEASUREMENT PROBE

(75) Inventor: Kent KinMan Tam, Rowland Heights, CA (US)

(73) Assignee: Northrop Grumman Corporation, Los Angeles, CA (US)

(*) Notice: Subject to any disclaimer, the term of this patent is extended or adjusted under 35 U.S.C. 154(b) by 99 days.

(21) Appl. No.: 10/293,648

(22) Filed: Nov. 13, 2002

(65) Prior Publication Data

US 2004/0100277 A1 May 27, 2004

(51) Int. Cl.[7] .................................................. G01R 27/32
(52) U.S. Cl. ........................ 324/633; 324/655; 324/693
(58) Field of Search ................................. 324/633, 655, 324/693, 635, 236

(56) References Cited

U.S. PATENT DOCUMENTS

| | | | |
|---|---|---|---|
| 3,931,571 A | * | 1/1976 | Hocking et al. ............. 324/236 |
| 4,005,359 A | | 1/1977 | Smoot |
| 4,286,216 A | | 8/1981 | Auld et al. |
| 4,364,012 A | | 12/1982 | Auld |
| 4,715,007 A | | 12/1987 | Fujita et al. |
| 5,508,610 A | * | 4/1996 | Feeney et al. ............... 324/719 |
| 5,514,337 A | * | 5/1996 | Groger et al. ............... 324/654 |
| 5,930,744 A | | 7/1999 | Koch et al. |
| 6,040,694 A | | 3/2000 | Becker |
| 6,184,694 B1 | | 2/2001 | Anderson et al. |
| 6,448,795 B1 | * | 9/2002 | Ermakov et al. ........... 324/724 |
| 6,462,538 B2 | * | 10/2002 | Harada ........................ 324/224 |

* cited by examiner

Primary Examiner—Anjan Deb
Assistant Examiner—Timothy J. Dole
(74) Attorney, Agent, or Firm—Stetina Brunda Garred & Brucker

(57) ABSTRACT

A non-contact probe for determining the conductivity of coating materials is disclosed. The probe includes a free running oscillator operating at a selected frequency, a sensor made up of an LC circuit, a detector for detecting a change in the LC circuit in response to change in the sensor coil induction, and a processor for converting the detected changes in the signal to surface conductivity data. The detector may be a frequency detector that detects changes in the resonant frequency of the LC circuit or the detector may be a magnitude detector that detects changes in the signal magnitude of the LC oscillator. The sensor is the coil inductor of the LC circuit. Inductance of the sensor coil is variable depending on conductivity of the material near the sensor coil.

51 Claims, 4 Drawing Sheets

NON-CONTACT SURFACE CONDUCTIVITY MEASUREMENT PROBE

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

The present invention relates generally to measuring devices and more particularly to an inductor-capacitor (LC) probe used for measuring surface conductivity.

Highly conductive coatings such as Indium Tin Oxide (ITO) are applied to glass/polycarbonate windshields and plastic lamp covers of stealth vehicles for scattering treatment of radar signals. For graphite and fiberglass composite surfaces, silver or similar conductive surfaces are extensively used. The electrical properties of these conductive coatings are characterized by surface resistance in ohms/square ($\Omega$/sq).

A four-point probe is a direct current (DC) resistance measurement device that requires direct contact with the conductive surface. When fabrication of these components is complete, the windshield ITO coating is protected with a urethane topcoat. The silver painted composite surface is painted with a urethane-based color paint. These topcoats insulate the conductive coating and inhibit electrical testing of the conductives using a four-point probe.

Silver paint has a service life of several years. Over time silver paint loses conductivity, e.g., due to oxidation. Routine and repair inspections of the coating's conductivity are required. Thus, there is a need for a way to measure a conductive layer's surface resistance through an insulating topcoat.

Surface gaps and seams are a major scattering source of radar signals. To suppress scattering of radar signals, surface gaps are typically filled with a conductive caulk. Most conductive caulks are made up of polymers and metal particles. Nickel particles are commonly used due to the low cost and chemical inertness. Shrinkage of the cured polymers consolidates the metal particles and brings DC conductivity upon the caulk. Since conductive caulk is installed in surface gaps, the caulk is subjected to ambient and mechanical agitation. Conductivity of the caulk degrades as the polymers age and lose their elasticity. The insulating color paint level prevents DC testing of the aging caulk. Inspection of the conductive caulk is further complicated by the nickel particles' magnetic properties. Neither eddy current nor magnetic induction is effective for moderately conductive, magnetic materials because eddy current in the conductor counteracts the magnetic induction produced by the metal's ferromagnetism. Thus, there is a need for a way to measure the conductivity of moderately conductive, ferromagnetic materials.

BRIEF SUMMARY OF THE INVENTION

A non-contact surface conductivity measurement probe for determining the conductivity of a material is disclosed. The probe includes an oscillator, a sensor made up of an LC circuit, a detector for detecting the response of the LC sensor circuit and a processor, such as a microprocessor, for converting the detected signal to surface conductivity. The detector may be a frequency counter that detects changes in the resonant frequency of the LC circuit or the detector may be an RF level detector that detects changes in the signal magnitude across the LC circuit. The LC circuit includes a capacitor (c) and a sensor coil (L). Inductance and dissipation factor of the sensor coil are varied depending on the conductivity and permeability of the material near the sensor coil.

Preferably, the oscillator and the LC sensor circuit are combined to form a free running oscillator. More preferably, the oscillator is a Colpitts oscillator circuit.

Preferably, the oscillator frequency is about 21 MHz.

In a typical application, the sensor coil is maintained at a fixed distance from the test surface. Surface resistance may be measured by a shift in the resonant frequency or a change in the oscillatory output level of the LC circuit. The shift in the resonant frequency or the signal magnitude is correlated to a set of known thin film resistance standards to yield the surface resistance of the test surface. The sensor's response to the thin film resistance standards may be stored in the processor circuit. In exemplary embodiments, the probe has a surface resistance range of about 0.01$\Omega$/sq to about 30$\Omega$/sq.

The test surface or target surface may be a non-magnetic conductive material. Measurement of the resonant frequency shift is the preferred detection method. If the material is a non-magnetic conductive material, a higher surface conductivity induces a higher eddy current on the conductor surface and a greater magnetic field is created. This magnetic field counteracts the sensor's driving field. Larger counteracting or opposing magnetic field results in larger resonant frequency shift (increase).

The test surface may be a ferromagnetic material. Measurement of the oscillator output level is the preferred detection method. If the material is a ferromagnetic material, a higher surface conductivity couples a heavier load to the LC circuit and results in a lower oscillator output level.

The probe may include a display device for displaying the conductivity measurement.

The test surface may comprise a Magnetic Radar Absorbing Material (MagRAM). Measurement of the resonant frequency shift is used to determine the thickness of the MagRAM coating. Thicker MagRAM coating increases the magnetic flux linkage and causes the sensor coil's inductance to increase. As a result, the resonant frequency decreases with larger MagRAM coating thickness. MagRAM may have a conductive or a non-conductive substrate. The MagRAM coating may be covered by a non-conductive paint coat.

BRIEF DESCRIPTION OF THE DRAWINGS

These, as well as other features of the present invention, will become more apparent upon reference to the drawings wherein.

DETAILED DESCRIPTION OF THE INVENTION

An Inductor-Capacitor (LC) probe 10 that shows sensitivity to the surface conductivity of coating materials is disclosed. The probe 10 measures output frequency or magnitude of an LC oscillator. The probe can be used to determine a conductive layer's surface resistance through an insulating topcoat, and an installed gap filler's conductivity. The probe can also be used to measure thicknesses of magnetic coatings such as the Magnetic Radar Absorbing Material (MagRAM) used in low observable surface treatments. Examples of applications of the probe include conductivity inspection of silver paint under insulating primer and paint coatings, installed conductive gap filler materials, the ITO coatings on windshields and lamps.

Figure 1:
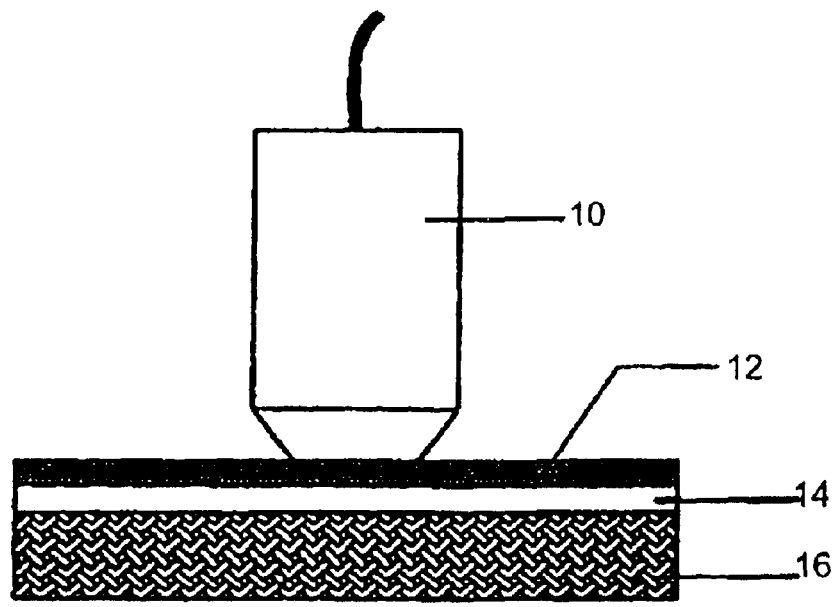
FIG. 1 is a typical configuration of a test surface for use with an LC probe formed in accordance with the present invention.

Referring now to the drawings wherein the showings are for purposes of illustrating preferred embodiments of the present invention only, and not for purposes of limiting the same, FIG. 1 illustrates a typical configuration of a test surface. The LC probe 10 is a handheld probe that is used to measure the surface resistance of a thin conductive layer 14 which is insulated by a non-conductive top coat 12. FIG. 1 shows a typical coating stack-up of the test surface. The topmost layer 12 is an insulating paint and/or primer layer. The middle layer 14 is a conductive layer which is the target of the test. The substrate 16 may be a non-conductive or conductive composite structure.

Figure 2:
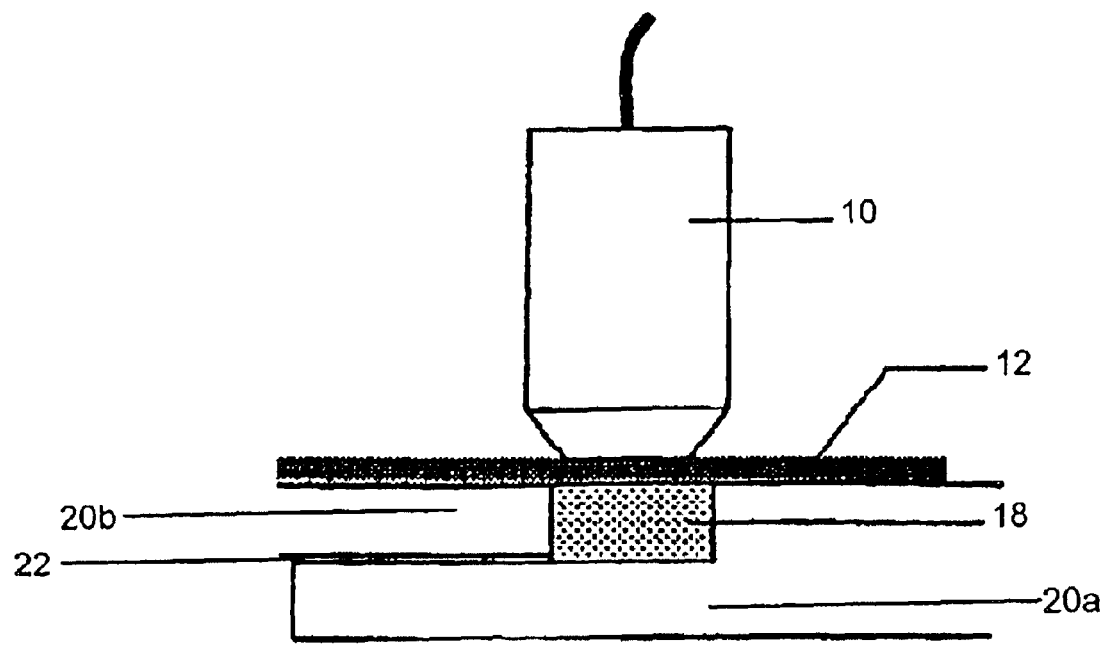
FIG. 2 illustrates a typical configuration of a conductive caulk-filled gap for use with the LC probe.

By measuring the LC oscillator output magnitude, the LC probe 10 has demonstrated an ability in detecting conductivity degradation in installed gap filler materials. The gap filler materials or conductive caulks are moderately conductive, magnetic or non-magnetic. FIG. 2 shows a typical configuration of a conductive caulk-filled gap. The insulating topcoat 12 consists of a color paint and primer layer. The conductive caulk 18 provides electrical continuity across the surface gap 22 between the conductive structures 20a and 20b to minimize scattering of radar signals. As the conductive caulk 18 loses its conductivity, its ability to suppress radar scattering degrades. Inspection of the conductive caulk 18 with the LC probe 10 would detect electrical failure of the material.

The LC probe's sensor coil has the ability to detect magnetic induction as well as eddy current, which enables the probe 10 to measure MagRAM thickness. By curve fitting several MagRAM samples of different thicknesses to the shift in the probe's resonant frequency, the sensor output can be translated to MagRAM thickness using the fitted curve.

The core of the LC probe sensor is a resonant circuit constructed with an inductor (L) and a capacitor (C). The inductor is a coil which is the sensing element. In one embodiment, the inductor is a 15 turn freestanding coil approximately 0.2" in diameter. Together with the parallel capacitor, a resonant circuit is formed. The resonant frequency (F) is given by:

$$F = \frac{1}{2\pi\sqrt{LC}} \quad (1)$$

It was found that a resonance frequency range of 10 MHz to 30 MHz yielded good sensitivity for medium to highly conductive surfaces (0.1 to 30Ω/sq).

Figure 3:
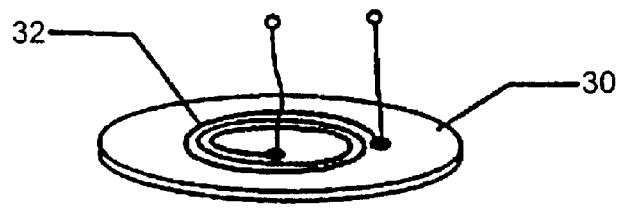
FIG. 3 is an illustration of a sensor coil etched on a printed circuit board.

In some embodiments, the sensor coil is etched on a printed circuit (PC) board to improve the compactness of the probe 10. The blank surface of the printed circuit board is the sensor surface. The planar coil is kept at a fixed offset distance from the test surface by the printed circuit board. In an exemplary embodiment, the thickness of the PC board is approximately 0.03" and the sensor is an 8-turn coil with a 0.5" outer diameter, tuned to a resonant frequency of 15 MHz. FIG. 3 shows an example of a sensor coil etched on a PC board. In the example shown, the etched coil 32 is copper trace that is etched on a PC board 30.

The LC probe 10 is sensitive to both the conductivity of the test surface and the distance from the test surface. Inconsistent topcoat or paint thickness can result in less accurate conductivity measurements. Preferably, the coil is kept at a large distance (0.030") relative to the paint thickness (~0.005") from the test surface by the printed circuit board so that the impact of slight topcoat thickness variation on surface conductivity measurement is lessened.

Other sensor coil configurations, such as coils wound on a ferrite rod and a C shaped ferrite core can be used to improve the compactness and sensitivity of the LC probe 10.

Figure 4:
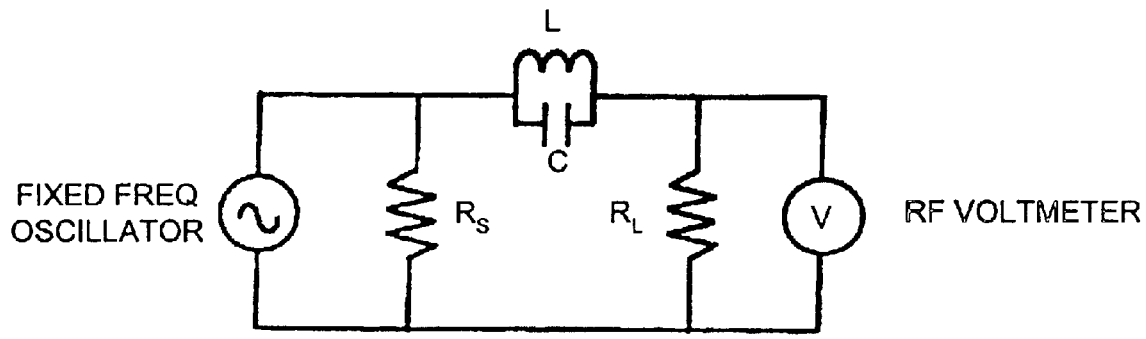
FIG. 4 illustrates a simplified circuit diagram of the LC probe.

FIG. 4 is a simplified circuit diagram of an embodiment of the LC probe. The LC circuit and the load resistor $R_L$ form a voltage divider, and feed a fraction of the fixed frequency oscillator signal to the RF voltmeter. With no conductive material in the proximity of the sensor coil, the LC circuit is tuned to resonate at the oscillator frequency. At resonance, the LC combination exhibits high circuit impedance. A small signal level will appear across the load resistor $R_L$. The voltage level is detected by the RF voltmeter. When the sensor coil is placed on a conductive surface, the magnetic field produced by the coil induces an eddy current in the conductive surface. This eddy current generates an opposing magnetic field that reduces the net flux density passing through the coil. As a result, the inductance of the sensor coil is lowered. The resonant frequency is thereby increased. When the resonant frequency of the LC circuit moves away from the fixed oscillator frequency, the impedance of the LC circuit is lowered. The voltage divider allows an increased amount of signal to reach the RF voltmeter. Higher surface conductivity will result in greater LC resonant deviation from the oscillator frequency and further lowering of the LC circuit impedance. The detected voltage is thus a measure of the detuning (shifting in frequency) in the LC circuit. When the sensor coil is maintained at a fixed distance from the conductive surface, the sensor output becomes a function of the surface's conductivity. The sensor output can be mapped to a set of known thin film resistance standards to yield equivalent readings in Ω/sq.

Similar to most eddy current conductivity test equipment, their calibrated conductivity or resistivity readings are not valid for ferromagnetic conductors. The foregoing detection scheme is only applicable to conductivity measurement of non-magnetic conductive materials.

Figure 5:
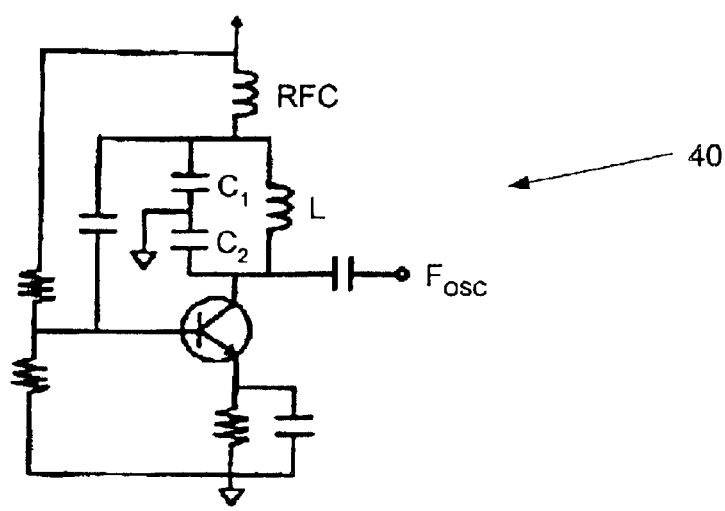
FIG. 5 illustrates a Colpitts oscillator forming an LC sensor.

When the sensor coil is in the vicinity of a ferromagnetic material, high magnetic permeability (p) of the material reduces the reluctance (magnetic resistance) between the two ends or poles of the coil by shortening the paths of the magnetic flux lines. The coil inductance is thus increased. In contrast with a non-magnetic conductive material, the LC resonance is shifted to a lower frequency instead. High permeability material will result in a large coil inductance increase. Sensor coils, which garner materials' magnetic properties by their inductance response, are known as magnetic induction sensors. A common application of these sensors is magnetic coating thickness measurements. To expand the utility of the LC sensor while maintaining a simple circuit design, the LC combination was re-reconfigured to form a free running oscillator as shown in FIG. 5. The oscillator circuit shown in FIG. 5 is a preferred configuration that uses a Colpitts oscillator due to its frequency range and output stability.

The oscillator frequency ($F_{OSC}$) is given by:

$$F_{OSC} = \frac{1}{2\pi\sqrt{LC_{EQ}}} \quad (2)$$

where $$C_{EQ} = C_1 // C_2$$

The nominal operating frequency is approximately 21 MHz. In the absence of a test target, the oscillator frequency and the output magnitude are measured and recorded as reference for subsequent calculations. When the sensor coil is placed on a non-magnetic conductive surface, the opposing field generated by the eddy current in the conductor will lower the coil inductance and raise the oscillator frequency ($F_{OSC}$).

Figure 6:
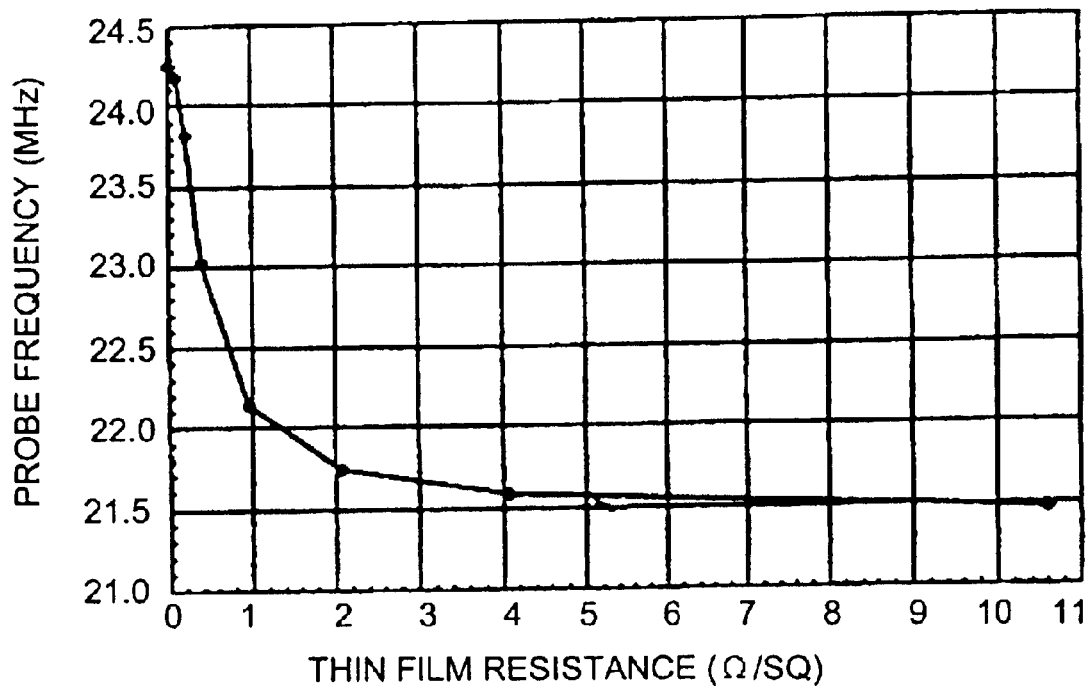
FIG. 6 is a graph illustrating the typical LC probe frequency response on a non-magnetic conductive thin film.

FIG. 6 is a graph showing the LC probe frequency as a function of non-magnetic thin film resistance. The LC probe shows extremely good sensitivity to surface resistance between 0.1Ω/sq to 4Ω/sq. Although the probe sensitivity drops off quickly as shown in FIG. 6, the probe frequency readings are stable to within 2 KHz. Therefore the probe yields acceptable resistivity sensitivity to approximately 30Ω/sq.

Figure 7:
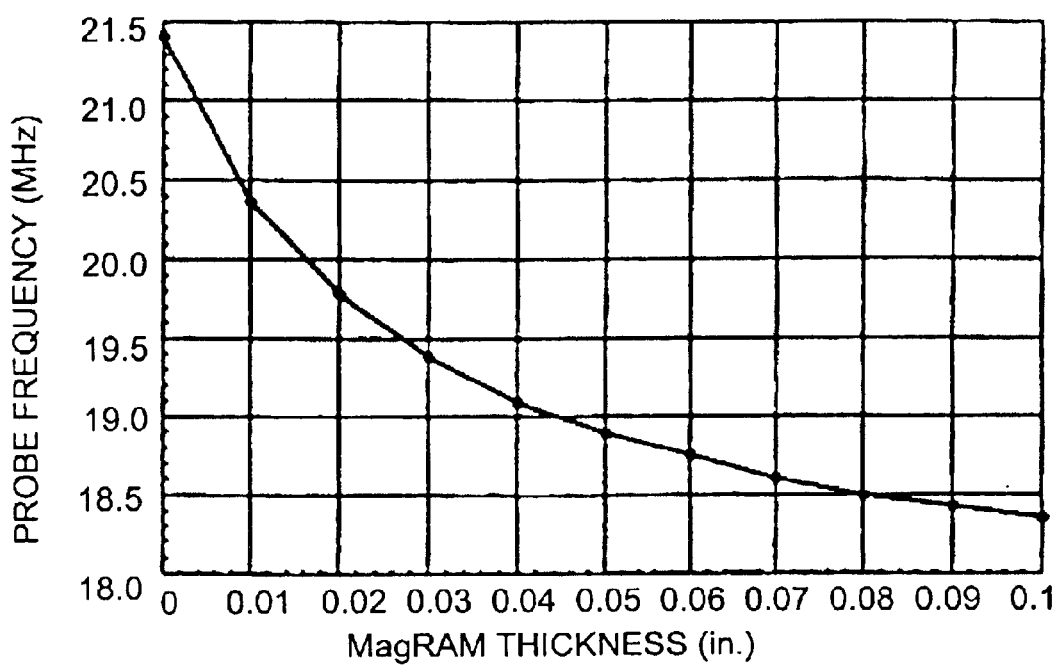
FIG. 7 is a graph illustrating the typical LC probe frequency response on a medium load MagRAM.

With a ferromagnetic conductor nearby, the coil inductance is raised and the oscillator frequency is lowered. The degree of frequency change is a function of the material's mass and permeability. Since the densities and permeability of most MagRAM are well controlled, the LC can therefore be used to measure MagRAM thickness. The LC probe response to thickness of a medium load MagRAM is shown in FIG. 7. When these measurements were taken, the test samples were supported by a piece of thick rigid dielectric foam so that the results were not influenced by the supporting substrate's electromagnetic properties.

Figure 8:
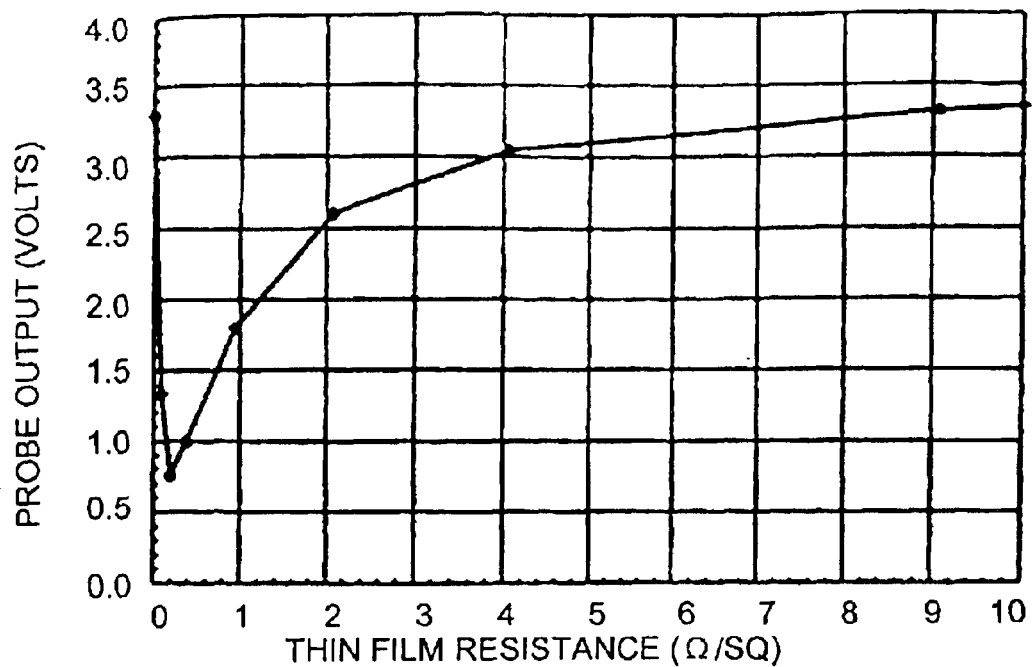
FIG. 8 is a graph illustrating the typical LC probe magnitude response on a non-magnetic conductive thin film.

The output level of the oscillator shown in FIG. 5 is a function of the sensor coil's Q factor. When a conductive surface (magnetic or non-magnetic) is brought to the vicinity of the sensor coil, a portion of the RF signal is inductively coupled into and dissipated by the conductor. The energy stored in the LC circuit is therefore reduced. From the circuit's standpoint, the internal resistance of coil is raised and the Q factor of the oscillator is lowered. As a result, the oscillator's output magnitude is lowered. FIG. 8 is a graph showing the LC probe output magnitude as a function of surface resistivity. The test data shown in FIG. 8 illustrates that from about 0.2Ω/sq to 40Ω/sq, the probe output increases monotonically with surface resistance. The output voltage shows a minimum point at about 0.2Ω/sq. The phenomenon infers that the amount of energy coupled and dissipated by the conductive surface peaks at about 0.2Ω/sq. Below 0.2Ω/sq, energy stored in the LC circuit can no longer be transferred and dissipated effectively due to the excessively small load impedance. To verify this postulation, a parallel LC circuit was connected to a sweep frequency impedance analyzer. The Q factor of the circuit showed a minimum when the coil was tested in the same surface resistance range. By excluding the left side of the minimum, the LC probe's monotonic magnitude response yields a mean for conductivity measurement of moderately conductive magnetic materials such as conductive caulks and fillers.

Figure 9:
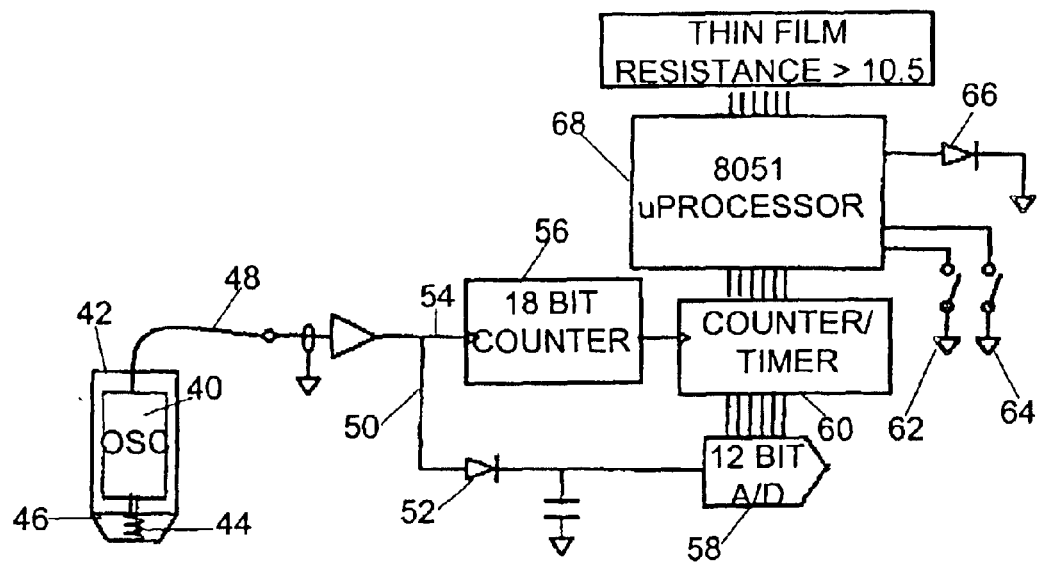
FIG. 9 is a block diagram of an exemplary LC probe.

FIG. 9 shows a block diagram of an exemplary embodiment of the LC probe 10. An oscillator 40, such as the one shown in FIG. 5, is integrated into a cylindrical probe housing 42. In preferred embodiments, the oscillator has an oscillator frequency of 21 MHz. A sensor coil 44 is encapsulated in the middle of a nylon cap 46 at the measurement end of the probe. The oscillator output is buffered and transmitted to the instrument box by a coax cable 48. Upon entering the instrument box, the RF signal is amplified and split into two paths. One path 50 leads to a diode detector 52. The other path 54 leads to an 18-bit counter 56. The diode detector 52 converts the amplitude of the 21 MHz RF signal into a DC voltage. The 18-bit counter 56 scales the RF signal to a digital signal below 10 KHz. These processed signals are then digitized by a 12-bit A/D 58 and a 16-bit timer/counter 60. The exemplary embodiment of the LC probe shown in FIG. 9 has two buttons: one button 62 scrolls through the available test functions, and the other button 64 is used to select a test function. A light emitting diode (LED) 66 serves as a GO/NO GO indicator when simple test criteria are met. Depending on the measurement selected (e.g., silver paint, ITO conductivity, MagRAM thickness), the probe frequency and/or the probe output magnitude may be acquired and passed to the appropriate processing routines. The logic for the processing routines is stored in a processor, for example, a microprocessor 68. An exemplary microprocessor is an 8051 microprocessor. The digital output may be displayed on a screen, such as a liquid crystal display (LCD).

Applications of the LC probe 10 include inspection of installed coating and caulking conductivity, and MagRAM thickness and uniformity. The probe 10 combines eddy current, magnetic induction, and energy coupling measurement capabilities in a single device. Its simple detection scheme eliminates the need for a complex magnitude and phase detection circuitry. Unlike the conventional eddy current and magnetic induction probes, the LC probe 10 achieves extended detection sensitivity by using a resonant type sensor. The probe's operating frequency, approximately 21 MHZ, is substantially higher than most conventional eddy current and magnetic induction probes.

Exemplary embodiments of the LC probe have a thin film resistivity measurement range of about 0.01Ω/sq to about 30 Ω/sq. The probe's small footprint and high operating frequency enable inspection of conductive filler materials with reduced interference from the adjacent structures. The LC probe is suitable for routine inspection of aging silver paint, repaired coatings, and conductive materials installed in 0.2" or wider gaps.

Most conductive gap filler and caulking materials are magnetic because they are loaded with nickel or nickel-coated particles. Their conductivities degrade as the materials age. Due to their high permeability and moderate conductivity, frequency shifts due to magnetic induction counteract and dominate the shifts caused by eddy current. Consequently, eddy current becomes ineffective or fails to quantify degradation of these conductive magnetic materials. The LC probe 10 approaches this problem by measuring dissipation of energy stored in the resonant circuit. Complication due to opposing effects on frequency shift is thus avoided.

Calibration of the LC probe 10 for thin film conductivity measurement is simple. A set of thin film standards ranging from 0.1Ω/sq to 40Ω/sq is measured. A fitted curve of the Ω/sq value as a function of the probe reading is created and programmed into the LC probe's micro-controller 68. This process rarely needs to be repeated unless the probe 10 or the electronics of the probe is repaired. Upon powering of the LC probe 10, a measurement of the probe output with no conductive or magnetic material nearby is acquired to adjust offsets in the detected voltage and frequency. After this measurement is made, the probe 10 is ready for use. No calibration standard is needed in routine use of the probe.

Different probe heads may be used in different embodiments of the probe. The various probe heads may differ in size.

Recent experiments have shown that the LC probe can be used to inspect conductive fiber mats. The fiber mats may be raw or impregnated with resin.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A non-contact surface conductivity measurement probe for conductivity measurement of a material having a conductive surface, the probe comprising:
   (a) an oscillator operating at a selected oscillator frequency;
   (b) a sensor comprising an LC circuit that is an integral part of the oscillator, the LC circuit including a sensor coil (L), inductance of the sensor coil being variable depending on conductivity of the material near the sensor coil;
   (c) a frequency detector for detecting a change in the resonant frequency of the LC circuit in response to change in the sensor coil induction;
   (d) a processor for converting detected changes in the resonant frequency to surface conductivity data; and
   (e) a spacer for maintaining the sensor coil at a fixed distance from the conductive surface.

2. The probe of claim 1, wherein the oscillator is a free running oscillator.

3. The probe of claim 2, wherein the free running oscillator is a Colpitts oscillator circuit.

4. The probe of claim 1, wherein the oscillator frequency is a radio frequency.

5. The probe of claim 4, wherein the oscillator frequency is about 21 MHz.

6. The probe of claim 1, wherein the probe is maintained at the fixed distance from the conductive surface-in order to determine a surface resistance measurement based on a shift in the resonant frequency.

7. The probe of claim 1, further comprising a display device for displaying output representative of the conductivity measurement.

8. A non-contact surface conductivity measurement probe for conductivity measurement of a material having a conductive surface, the probe comprising:
   (a) an oscillator operating at a selected oscillator frequency;
   (b) a sensor comprising an LC circuit that is an integral part of the oscillator, the LC circuit including a sensor coil (L), inductance of the sensor coil being variable depending on conductivity of the material near the sensor coil;
   (c) a frequency detector for detecting a change in the resonant frequency of the LC circuit in response to change in the sensor coil induction; and
   (d) a processor for converting detected changes in the resonant frequency to surface conductivity data;
   wherein the sensor coil is maintained at a fixed distance from the conductive surface—in order to determine a surface resistance measurement based on a shift in the resonant frequency, the shift in the resonant frequency being mapped to a set of known thin film resistance standards to yield the surface resistance measurement as an equivalent reading in Ω/sq.

9. The probe of claim 8, wherein the set of known thin film resistance standards is stored in the processor.

10. The probe of claim 8, wherein the probe has a surface resistance range of about 0.01Ωsq to about 30Ω/sq.

11. The probe of claim 8, wherein the material is a non-magnetic conductive material.

12. The probe of claim 8, wherein the material is a ferromagnetic material.

13. A non-contact surface conductivity measurement probe for conductivity measurement of a material, the probe comprising:
   (a) an oscillator operating at a selected oscillator frequency;
   (b) a sensor comprising an LC circuit that is an integral part of the oscillator, the LC circuit including a sensor coil (L), inductance of the sensor coil being variable depending on conductivity of the material near the sensor coil;
   (c) a frequency detector for detecting a change in the resonant frequency of the LC circuit in response to change in the sensor coil induction; and
   (d) a processor for converting detected changes in the resonant frequency to surface conductivity data;
   wherein a MagRAM coating is applied on top of the material and the conductivity measurement is used to determine a thickness of the MagRAM coating by magnetic induction.

14. The probe of claim 13, wherein the material has a conductive substrate.

15. The probe of claim 13, wherein the material has non-conductive substrate.

16. The probe of claim 13, wherein the MagRAM coating is covered by a non-conductive paint coat.

17. A non-contact surface conductivity measurement probe for conductivity measurement of a material having a conductive surface, the probe comprising:
   (a) an oscillator operating at a selected oscillator frequency;
   (b) a sensor comprising an LC circuit that is an integral part of the oscillator, the LC circuit including a sensor coil (L), inductance of the sensor coil being variable depending on conductivity of the material near the sensor coil;
   (c) a signal magnitude detector for detecting a change in the signal magnitude of the LC circuit in response to change in the sensor coil induction;
   (d) a processor for converting detected changes in the signal magnitude to surface conductivity data; and (e) a spacer for maintaining the sensor coil at a fixed distance from the conductive surface.

18. The probe of claim 17, wherein the oscillator is a free running oscillator.

19. The probe of claim 18, wherein the free running oscillator is a Colpitts oscillator circuit.

20. The probe of claim 17, wherein the oscillator frequency is a radio frequency.

21. The probe of claim 20, wherein the oscillator frequency is about 21 MHz.

22. The probe of claim 17, wherein the probe is maintained at the fixed distance from the conductive surface in order to determine a surface resistance measurement based on a shift in the signal magnitude.

23. The probe of claim 17, further comprising a display device for displaying output representative of the conductivity measurement.

24. A non-contact surface conductivity measurement probe for conductivity measurement of a material having a conductive surface, the probe comprising:

(a) an oscillator operating at a selected oscillator frequency;

(b) a sensor comprising an LC circuit that is an integral part of the oscillator, the LC circuit including a sensor coil (L), inductance of the sensor coil being variable depending on conductivity of the material near the sensor coil;

(c) a signal magnitude detector for detecting a change in the signal magnitude of the LC circuit in response to change in the sensor coil induction; and (d) a processor for converting detected changes in the signal magnitude to surface conductivity data;

wherein the material has a conductive surface and the sensor coil is maintained at a fixed distance from the conductive surface in order to determine a surface resistance measurement based on a shift in the signal magnitude, the shift in the signal magnitude being mapped to a set of known thin film resistance standards to yield the surface resistance measurement as an equivalent reading in $\Omega$/sq.

25. The probe of claim 24, wherein the set of known thin film resistance standards is stored in the processor.

26. The probe of claim 24, wherein the probe has a surface resistance range of about 0.01$\Omega$/sq to about 30$\Omega$/sq.

27. The probe of claim 24, wherein the material is a non-magnetic conductive material.

28. The probe of claim 24, wherein the material is a ferromagnetic material.

29. A non-contact surface conductivity measurement probe for conductivity measurement of a material, the probe comprising:

(a) an oscillator operating at a selected oscillator frequency;

(b) a sensor comprising an LC circuit that is an integral part of the oscillator, the LC circuit including a sensor coil (L), inductance of the sensor coil being variable depending on conductivity of the material near the sensor coil;

(c) a signal magnitude detector for detecting a change in the signal magnitude of the LC circuit in response to change in the sensor coil induction; and (d) a processor for converting detected changes in the signal magnitude to surface conductivity data;

wherein a MagRAM coating is applied on top of the material and the conductivity measurement is used to determine a thickness of the MagRAM coating by using magnetic induction to measure dissipation of energy stored in the LC circuit.

30. The probe of claim 29, wherein the material has a non-conductive surface.

31. The probe of claim 29, wherein the MagRAM coating is covered by a non-conductive paint coat.

32. A non-contact surface conductivity measurement probe for conductivity measurement of a material having a test surface, the probe comprising:

(a) an oscillator operating at a selected oscillator frequency;

(b) a sensor comprising an LC circuit that is an integral part of the oscillator, the LC circuit including a generally planar sensor coil (L), inductance of the sensor coil being variable depending on conductivity of the material near the sensor coil, the sensor coil being etched on a printed circuit (PC) board such that the sensor coil is maintained at a fixed distance from the test surface by the printed circuit board;

(c) a frequency detector for detecting a change in the resonant frequency of the LC circuit in response to change in the sensor coil induction; and (d) a processor for converting detected changes in the resonant frequency to surface conductivity data.

33. The probe of claim 32 wherein the thickness of the PC board is a proximately 0.03 inch and having a blank surface that interfaces with the test surface.

34. The probe of claim 32 wherein the sensor coil is an 8-turn coil tuned to a resonant frequency of about 15 MHz.

35. The probe of claim 32 wherein the etched sensor coil is copper trace.

36. The probe of claim 32 wherein the etched sensor coil has an outer diameter of about 0.5 inch.

37. The probe of claim 32 wherein the etched sensor coil has a generally spiral configuration on the PC board.

38. The probe of claim 32, wherein the oscillator is a free running oscillator.

39. The probe of claim 38, wherein the free running oscillator is a Colpitts oscillator circuit.

40. The probe of claim 32, wherein the oscillator frequency is a radio frequency.

41. The probe of claim 40, wherein the oscillator frequency is about 21 MHz.

42. The probe of claim 32, wherein the sensor coil is maintained at a fixed distance from the test surface in order to determine a surface resistance measurement based on a shift in the resonant frequency.

43. The probe of claim 42, wherein the shift in the signal magnitude is mapped to a set of known thin film resistance standards to yield the surface resistance measurement as an equivalent reading in $\Omega$/sq.

44. The probe of claim 43, wherein the set of known thin film resistance standards is stored in the processor.

45. The probe of claim 43, wherein the probe has a surface resistance range of about 0.01$\Omega$/sq to about 30$\Omega$/sq.

46. The probe of claim 43, wherein the material is a non-magnetic conductive material.

47. The probe of claim 43, wherein the material is a ferromagnetic material.

48. The probe of claim 32, further comprising a display device for displaying output representative of the conductivity measurement.

49. The probe of claim 32, wherein a MagRAM coating is applied on top of the material and the conductivity measurement is used to determine a thickness of the MagRAM coating by using magnetic induction to measure dissipation of energy stored in the LC circuit.

50. The probe of claim 49, wherein the material has a non-conductive surface.

51. The probe of claim 49, wherein the MagRAM coating covered by a non-conductive paint coat.

* * * * *